United States Patent
Watanabe et al.

(10) Patent No.: US 10,550,274 B2
(45) Date of Patent: Feb. 4, 2020

(54) ANTIBACTERIAL/ANTIVIRAL COATING AGENT

(71) Applicant: LIXIL CORPORATION, Tokyo (JP)

(72) Inventors: Yoichi Watanabe, Tokyo (JP); Hiroshi Kakehi, Tokyo (JP); Yuki Shuto, Tokyo (JP)

(73) Assignee: Lixil Corporation, Tokyo (JP)

( * ) Notice: Subject to any disclaimer, the term of this patent is extended or adjusted under 35 U.S.C. 154(b) by 63 days.

(21) Appl. No.: 15/574,066

(22) PCT Filed: Jun. 28, 2016

(86) PCT No.: PCT/JP2016/069085
§ 371 (c)(1),
(2) Date: Nov. 14, 2017

(87) PCT Pub. No.: WO2017/002787
PCT Pub. Date: Jan. 5, 2017

(65) Prior Publication Data
US 2018/0291214 A1    Oct. 11, 2018

(30) Foreign Application Priority Data
Jul. 1, 2015 (JP) ................. 2015-132847

(51) Int. Cl.
*C09D 7/63* (2018.01)
*A01N 33/12* (2006.01)
(Continued)

(52) U.S. Cl.
CPC .............. *C09D 7/63* (2018.01); *A01N 25/04* (2013.01); *A01N 25/10* (2013.01); *A01N 33/12* (2013.01);
(Continued)

(58) Field of Classification Search
CPC ......... A01N 33/12; C09D 133/00; C09D 5/14
See application file for complete search history.

(56) References Cited

U.S. PATENT DOCUMENTS 4,847,088 A    7/1989  Blank
9,943,081 B2 *  4/2018  Watanabe .............. A01N 37/10
(Continued)

FOREIGN PATENT DOCUMENTS

CN    1431255 A    7/2003
CN    1687305 A    10/2005
(Continued)

OTHER PUBLICATIONS

Machine translated English language equivalent of JP 2013071031 (2013, 7 pages).*
(Continued)

*Primary Examiner* — Brieann R Johnston
(74) *Attorney, Agent, or Firm* — Muncy, Geissler, Olds & Lowe, P.C.

(57) ABSTRACT

The purpose of the present invention is to provide an antibacterial/antiviral coating agent capable of forming an antibacterial/antiviral coating film that can maintain an excellent appearance. This antibacterial/antiviral coating agent includes acrylic melamine paint, a quaternary ammonium salt, polyvalent carboxylic acid, and phosphoric acid; the quaternary ammonium salt is included at over 3.0 parts by weight and under 5.0 parts by weight to 100 parts by weight of acrylic melamine paint solids, and the phosphoric acid is included at a mole ratio of 0.5-3.5 to the quaternary ammonium salt.

4 Claims, 4 Drawing Sheets

(51) Int. Cl.
*C09D 5/14* (2006.01)
*A01N 25/04* (2006.01)
*C09D 7/61* (2018.01)
*A01N 25/10* (2006.01)
*C09D 133/08* (2006.01)
*C08K 5/092* (2006.01)
*C08K 5/19* (2006.01)
*C08K 3/32* (2006.01)

(52) U.S. Cl.
CPC .................. *C09D 5/14* (2013.01); *C09D 7/61* (2018.01); *C09D 133/08* (2013.01); *C08K 5/092* (2013.01); *C08K 5/19* (2013.01); *C08K 2003/329* (2013.01)

(56) References Cited

U.S. PATENT DOCUMENTS

| | | |
|---|---|---|
| 2005/0215639 A1 | 9/2005 | Mohr et al. |
| 2007/0237901 A1 | 10/2007 | Moses et al. |
| 2010/0115706 A1 | 5/2010 | Bender |
| 2016/0205929 A1 | 7/2016 | Watanabe et al. |

FOREIGN PATENT DOCUMENTS

| | | |
|---|---|---|
| CN | 1320079 C | 6/2007 |
| CN | 101394747 A | 3/2009 |
| CN | 101486863 A | 7/2009 |
| CN | 101589189 A | 11/2009 |
| CN | 102505467 A | 6/2012 |
| JP | H01265594 A | 10/1989 |
| JP | H01313408 A | 12/1989 |
| JP | H03-069670 A | 3/1991 |
| JP | H10-265594 A | 10/1998 |
| JP | 2000-191409 A | 7/2000 |
| JP | 2005527609 A | 9/2005 |
| JP | 2008-189596 A | 8/2008 |
| JP | 2009055960 A | 3/2009 |
| JP | 2009-528326 A | 8/2009 |
| JP | 2010-083830 A | 4/2010 |
| JP | 2010-195782 A | 9/2010 |
| JP | 2011058136 A | 3/2011 |
| JP | 2011072868 A | 4/2011 |
| JP | 2012071893 A | 4/2012 |
| JP | 2012176279 A | 9/2012 |
| JP | 2013-071031 A | 4/2013 |
| JP | 2013-071893 A | 4/2013 |
| JP | 2015-067658 A | 4/2015 |
| WO | WO2011/089840 A1 | 7/2011 |
| WO | WO2013/047642 A1 | 4/2013 |
| WO | WO2014/008264 A1 | 1/2014 |
| WO | WO 2015046372 A1 | 4/2015 |

OTHER PUBLICATIONS

Machine translated English language equivalent of 2015-067658 (2015, 6 pages).*
Catinal STC-80, Toho Chemical Industry, 2019, 2 pages.*
Polymer Solutions. Heat Stabilizers: The coolest Polymer Additive. 2015 https://www.polymersolutions.com/blog/heat-stabilizer-analysis/.

* cited by examiner

ANTIBACTERIAL/ANTIVIRAL COATING AGENT

TECHNICAL FIELD

The present invention relates to an antibacterial/antiviral coating agent capable of forming an antibacterial/antiviral coating film which can maintain an excellent appearance.

BACKGROUND ART

In recent years, antibacterial/antiviral coating films have been applied to a wide variety of products as the awareness of hygiene concept and beauty in the living environment has increased. Generally in order to add antibacterial/antiviral properties to a coating film, it is a known method to form a coating film using a paint to which an effective amount a quaternary ammonium salt is added.

However, in the case of using an antibacterial/antiviral coating film in a member for wet area such as a kitchen sink or a faucet handle of a bathroom, the water resistance of the coating film is a problem. With regard to this, when a coating film to which a quaternary ammonium salt was added comes into contact with water, it is concerned that the quaternary ammonium salt dissolves out therefrom and the antibacterial/antiviral properties thereof are thus impaired. In order to solve this problem, an invention is described in Patent Document 1 that can suppress dissolution out of the quaternary ammonium salt from the coating film and can form an antibacterial/antiviral coating film exhibiting excellent water resistance by adding a polyvalent carboxylic acid to the paint together with a quaternary ammonium salt.

Incidentally, an acrylic melamine paint is often used as a paint for construction members, but it has been concerned that poor curing of the coating film occurs and a high surface hardness and high solvent resistance are not obtained when a quaternary ammonium salt is added to an acrylic melamine paint. In order to solve this problem, it is described in Patent Document 2 that it is possible to eliminate poor curing of the coating film caused by the addition of a quaternary ammonium salt by adding phosphoric acid as a curing accelerator of the coating film to the acrylic melamine paint together with a quaternary ammonium salt.

[Patent Document 1] Japanese Unexamined Patent Application, Publication No. 2015-67658

[Patent Document 2] Japanese Unexamined Patent Application, Publication No. 2013-71031

DISCLOSURE OF THE INVENTION

Problems to be Solved by the Invention

However, in the case of simply adding a quaternary ammonium salt and phosphoric acid to the acrylic melamine paint, a precipitate is generated in the paint and poor appearance of the coating film due to the precipitate is obtained in some cases.

The present invention has been made in view of the above circumstances, and an object thereof is to provide an antibacterial/antiviral coating agent capable of forming an antibacterial/antiviral coating film which can maintain an excellent appearance.

Means for Solving the Problems

(1) In order to achieve the above object, the present invention provides an antibacterial/antiviral coating agent containing an acrylic melamine paint, a quaternary ammonium salt, a polyvalent carboxylic acid, and phosphoric acid, in which the quaternary ammonium salt is contained at over 3.0 parts by mass and under 5.0 parts by mass with respect to 100 parts by mass of solids in the acrylic melamine paint and phosphoric acid is contained at from 0.50 to 3.5 in a mole ratio with respect to the quaternary ammonium salt.

(2) In the antibacterial/antiviral coating agent according to the invention of (1), it is preferable that the quaternary ammonium salt is contained at from 3.5 to 4.5 parts by mass with respect to 100 parts by mass of solids in the acrylic melamine paint.

(3) In the antibacterial/antiviral coating agent according to the invention of (1) or (2), it is preferable that phosphoric acid is contained at from 0.75 to 1.77 in a mole ratio with respect to the quaternary ammonium salt.

(4) In the antibacterial/antiviral coating agent according to any invention of (1) to (3), it is preferable that the quaternary ammonium salt is a quaternary ammonium salt represented by the following Formula (1).

[formula 01]

(1)

(In Formula (1), $R^1$ represents an alkyl group and $R^{2A}$, $R^{2B}$, and $R^{2C}$ each independently represent an alkyl group having from 1 to 3 carbon atoms. X represents a halogen atom.)

(5) In the antibacterial/antiviral coating agent according to any invention of (1) to (4), it is preferable that the polyvalent carboxylic acid is an aromatic polyvalent carboxylic acid.

Effects of the Invention

According to the antibacterial/antiviral coating agent of the present invention, it is possible to form an antibacterial/antiviral coating film which can maintain an excellent appearance and also exhibits excellent water resistance.

PREFERRED MODE FOR CARRYING OUT THE INVENTION

Hereinafter, embodiments of the present invention will be described. It should be noted that the present invention is not limited to the following embodiments.

<Antibacterial/Antiviral Coating Agent>

The antibacterial/antiviral coating agent of the present embodiment contains an acrylic melamine paint, a quaternary ammonium salt, a polyvalent carboxylic acid, and phosphoric acid. Hereinafter, the respective components will be described in detail.

[Quaternary Ammonium Salt]

Quaternary ammonium salts are widely used as an antibacterial/antiviral component because of their high antibacterial/antiviral properties, high safety, and easy migration to the surface. Particularly, those having the structure represented by the following Formula (1) are preferably used. In addition, in the following Formula (1), $R^1$ is preferably an alkyl group having from 8 to 22 carbon atoms, particularly from 16 to 18 carbon atoms, and $R^{2A}$, $R^{2B}$, and $R^{2C}$ are preferably a methyl group. Examples of X may include a chlorine atom and a bromine atom.

[formula 02]

(1)

(In Formula (1), $R^1$ represents an alkyl group and $R^{2A}$, $R^{2B}$, and $R^{2C}$ each independently represent an alkyl group having from 1 to 3 carbon atoms. X represents a halogen atom.)

Examples of the quaternary ammonium salt represented by Formula (1) may include dodecyltrimethylammonium chloride ($R^1=C_{12}H_{25}$), hexadecyltrimethylammonium chloride ($R^1=C_{16}H_{33}$), and octadecyltrimethylammonium chloride ($R^1=C_{18}H_{37}$). These may be used singly or in mixture of two or more kinds thereof. In addition, among these, it is particularly preferable to use octadecyltrimethylammonium chloride, and hexadecyltrimethylammonium chloride from the viewpoint of antibacterial/antiviral properties and safety.

[Polyvalent Carboxylic Acid]

A polyvalent carboxylic acid forms an ionically bonded body as the carboxyl group thereof ionically bonds with the quaternary ammonium group of a quaternary ammonium salt of an antibacterial/antiviral component. At this time, two or more quaternary ammonium salts are bonded to one polyvalent carboxylic acid to form an ionically bonded body having a large molecular weight in the antibacterial/antiviral coating film as the polyvalent carboxylic acid has two or more carboxyl groups. This ionically bonded body having a large molecular weight does not readily dissolve out from the coating film even in the case of coming into contact with water but is stably held in the antibacterial/antiviral coating film, and deterioration in antibacterial/antiviral properties by being wet with water is thus prevented.

In order to form an ionically bonded body having a large molecular weight in this manner, the number of carboxyl groups of the polyvalent carboxylic acid is required to be 2 or more. The number of carboxyl groups of the polyvalent carboxylic acid is preferably about from 2 to 4 in particular.

In addition, it is impossible to form an antibacterial/antiviral coating film exhibiting excellent water resistance when the number of carbon atoms of the hydrocarbon group of the polyvalent carboxylic acid is 5 or fewer. The upper limit of the number of carbon atoms of the hydrocarbon group is not particularly limited, but it is usually 20 or fewer from the viewpoint of handling properties and availability.

The hydrocarbon group of a polyvalent carboxylic acid is preferably an aromatic group since it is possible to form an ionically bonded body which is structurally stable as well. The polyvalent carboxylic acid is particularly preferably an aromatic polyvalent carboxylic acid in which two or more carboxyl groups are bonded to an aromatic hydrocarbon ring. Specific examples of the aromatic polyvalent carboxylic acid may include pyromellitic acid and trimesic acid. Trimesic acid is particularly preferably used.

In the case of a polyvalent carboxylic acid in which carboxyl groups are bonded in the radial direction as these aromatic polyvalent carboxylic acids, the carboxyl groups thereof are separated from each other and thus a quaternary ammonium salt is easily bonded thereto and a stable high molecular weight ionically bonded body can be formed. These polyvalent carboxylic acids may be used singly or in mixture of two or more kinds thereof.

[Phosphoric Acid]

Phosphoric acid functions as a curing accelerator of the coating film. Curing of the coating film is inhibited when a quaternary ammonium salt is added to an acrylic melamine paint. There is a possibility to cause a decrease in surface hardness and solvent resistance of the coating film as curing of the coating film is inhibited, but poor curing of the coating film is eliminated by adding phosphoric acid as a curing accelerator, whereby these problems can be solved.

The mechanism by which phosphoric acid functions as a curing accelerator of coating film is not necessarily clear, but, for example, the following mechanism is conceivable. First, in a case in which phosphoric acid is not added to the acrylic melamine paint, the reaction between the acrylic resin and the melamine resin is inhibited by the electrical interaction between the quaternary ammonium salt having a positive charge and the acrylic resin having a negative charge in the acrylic melamine paint. Here, in a case in which phosphoric acid is added to the acrylic melamine paint as in the present embodiment, it is presumed that phosphoric acid having a negative charge neutralizes the charge of the quaternary ammonium salt so as to play a role of preventing the reaction inhibition of the resin by the quaternary ammonium salt as described above.

Examples of a compound having a function as a curing accelerator of an acrylic melamine coating film may include dibutyltin dioxide, m-xylene-4-sulfonic acid, dodecylbenzenesulfonic acid, methanesulfonic acid, and n-methylpiperidine in addition to phosphoric acid, but phosphoric acid is most preferably used among these. Hereinafter, the fact that phosphoric acid is excellent as a curing accelerator of an acrylic melamine coating film will be described with reference to Table 1.

TABLE 01

| Acidic substance | Amount added (quaternary ammonium salt ratio) Mole ratio | Rubbing test | | Judgment |
| --- | --- | --- | --- | --- |
| | | ΔE | Gloss maintenance (%) | |
| Nil | 0.00 | 0.8 | 23.3% | 0 |
| Dibutyltin dioxide | 0.09 | 0.3 | 69.2% | 1 |
| | 0.14 | 0.1 | 93.7% | 2 |
| Phosphoric acid | 0.32 | 0.1 | 108.6% | 2 |
| | 0.48 | 0.1 | 115.5% | 2 |

TABLE 01-continued

| Acidic substance | Amount added (quaternary ammonium salt ratio) Mole ratio | Rubbing test | | |
|---|---|---|---|---|
| | | ΔE | Gloss maintenance (%) | Judgment |
| | 0.97 | 0.1 | 148.3% | 2 |
| | 1.61 | 0.1 | 186.0% | 2 |
| m-xylene-4-sulfonic acid | 0.17 | 0.3 | 52.6% | 1 |
| | 0.25 | 0.2 | 94.3% | 2 |
| | 0.51 | 1.1 | 87.5% | 2 |
| Dodecylbenzenesulfonic acid | 0.10 | 1.4 | 40.1% | 0 |
| | 0.15 | 0.4 | 63.6% | 0 |
| Methanesulfonic acid | 0.33 | 0.2 | 55.9% | 0 |
| | 0.49 | 0.6 | 74.6% | 0 |
| n-methylpiperidine | 0.32 | 0.4 | 48.1% | 0 |
| | 0.48 | 0.5 | 46.5% | 0 |

Table 1 is a table to compare the curability of coating films in a case in which various kinds of acidic substances are added to an acrylic melamine paint containing a quaternary ammonium salt at 4% by weight with respect to 100 parts by mass of the solids in the paint. For example, as presented in Table 1, the curability of coating film is evaluated by the judgement on ΔE, gloss maintenance (%), and appearance after a rubbing test. The rubbing test is conducted by strongly rubbing the surface of a coating film 5 times with a waste cloth impregnated with ethanol. The judgment is made according to the criteria of no change in appearance (2), a slight change in appearance (1), and a change in appearance (0). As presented in Table 1, it can be seen that the results of judgment on ΔE and gloss maintenance (%) after the rubbing test of the coating film formed by an acrylic melamine paint to which phosphoric acid is added are both more favorable as compared to those of the coating films to which other acidic substances are added, and the curability of the coating films is higher. Hence, it can be said that phosphoric acid has a higher function as a curing accelerator of an acrylic melamine coating film than other acidic substances.

[Acrylic Melamine Paint]

An acrylic melamine paint is preferably used as a paint for building members since it exhibits excellent adhesive properties to various kinds of metal materials and excellent chemical resistance and contamination resistance. The acrylic melamine paint contains an acrylic resin as a base material and a melamine resin as a crosslinking agent. The acrylic melamine paint of the present embodiment may be either of a solvent-based one or a water-based one.

[Proportion of Respective Components Contained]

In the antibacterial/antiviral coating agent according to the present embodiment, the proportion of the quaternary ammonium salt contained is over 3.0 parts by mass and under 5.0 parts by mass with respect to 100 parts by mass of the solids in the paint. The coating film formed tends to be inferior in antibacterial/antiviral properties in a case in which the quaternary ammonium salt is 3.0 parts by mass or less with respect to 100 parts by mass of the solids in the paint. A precipitate is generated in the coating agent and the appearance of the coating film deteriorates in a case in which the quaternary ammonium salt is 5.0 parts by mass or more. A more preferable range thereof is from 3.5 to 4.5 parts by mass.

In addition, in the antibacterial/antiviral coating agent according to the present embodiment, the proportion of phosphoric acid contained is from 0.5 to 3.5 in a mole ratio with respect to the quaternary ammonium salt. The coating film formed is poorly cured and the surface hardness and solvent resistance thereof decrease in a case in which the proportion of phosphoric acid contained is under 0.5 in a mole ratio with respect to the quaternary ammonium salt. In addition, phosphoric acid does not exert a superior effect as a curing accelerator of the coating film even when the proportion of phosphoric acid contained exceeds 3.5 in a mole ratio with respect to the quaternary ammonium salt. A more preferable range thereof is from 0.75 to 1.77 in a mole ratio.

Figure 1:
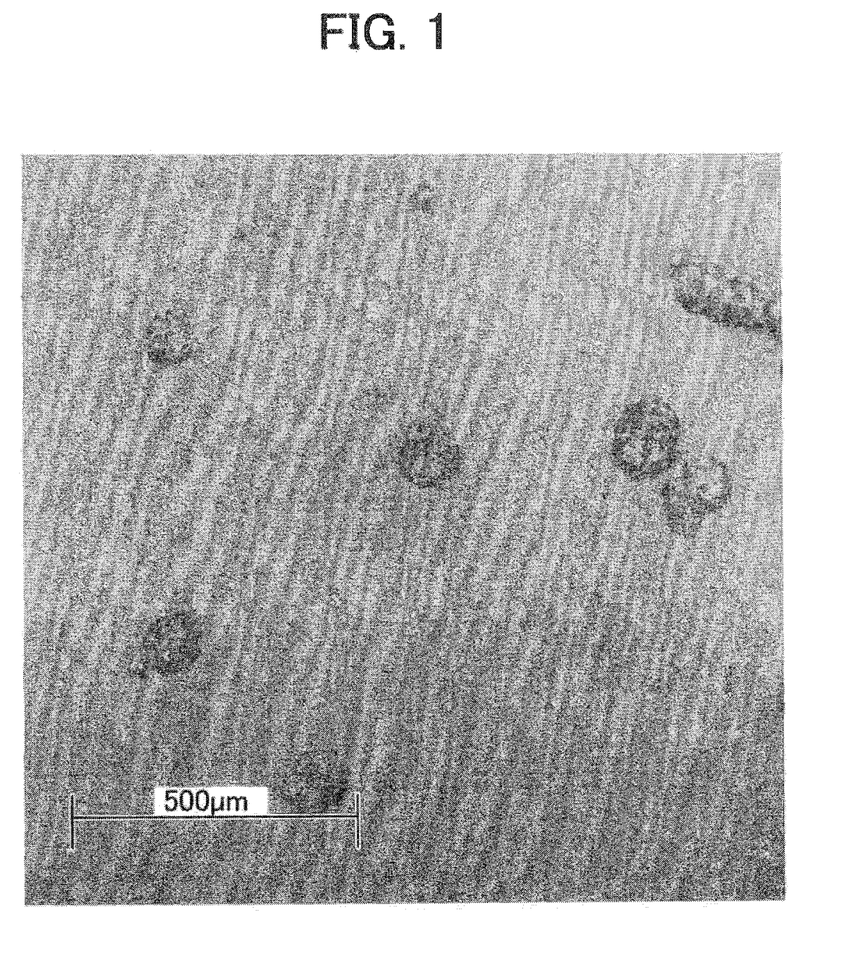
FIG. 1 is a photomicrograph illustrating a precipitate generated in a coating agent in which phosphoric acid is added to a conventional coating agent.

When phosphoric acid is added to a coating agent containing a conventional quaternary ammonium salt, a precipitate is generated in the coating agent depending on the amounts of the quaternary ammonium salt and phosphoric acid and a defective appearance of the coating film due to the precipitate is generated in some cases. FIG. 1 is a photomicrograph illustrating a precipitate generated in a coating agent in which phosphoric acid is added to a conventional coating agent containing a large amount of a quaternary ammonium salt. As is apparent from FIG. 1, a precipitate having a size larger than 100 µm is generated and it is considered that such a precipitate causes a defective appearance of the coating film.

Figure 2:
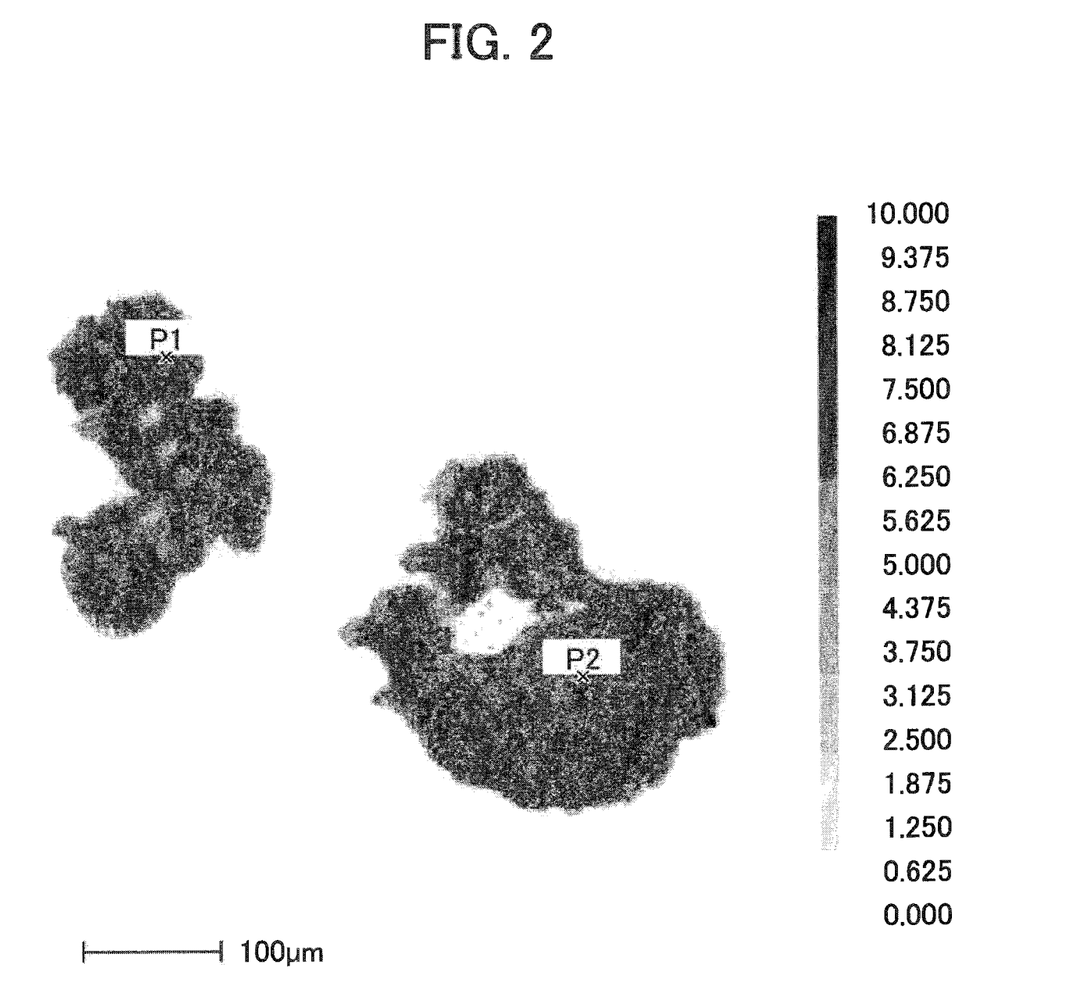
FIG. 2 is a diagram illustrating the results on EPMA analysis representing the concentration distribution of phosphorus in the precipitate according to FIG. 1.

In addition, the results on element analysis of the precipitate using EPMA are illustrated in FIG. 2. In FIG. 2, the vertical axis represents the relative concentration distribution of phosphorus and the relative concentrations at points P1 and P2 are 7.074 and 6.668, respectively. As is apparent from FIG. 2, a large amount of phosphorus is contained in the precipitate generated. Although the mechanism by which such a precipitate is generated is not clear, it is presumed that phosphoric acid cannot sufficiently neutralize the charge of the quaternary ammonium salt when a quaternary ammonium salt is present in a large amount, aggregation of the quaternary ammonium salt with phosphoric acid occurs, and a precipitate is generated.

Figure 3:
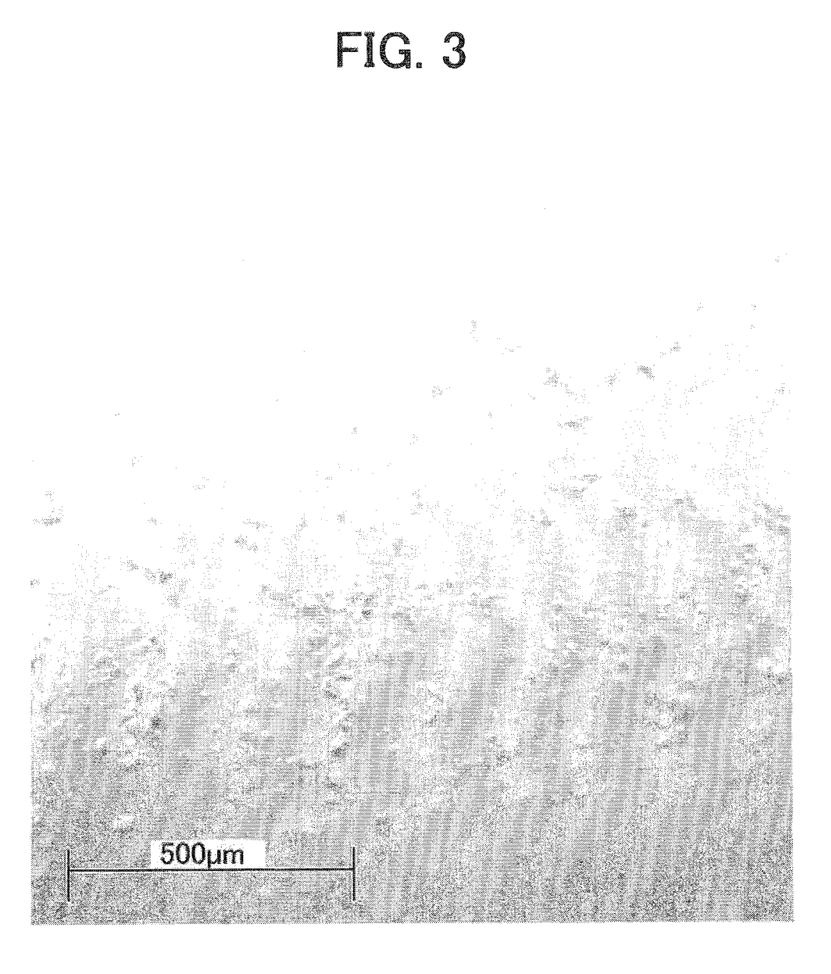
FIG. 3 is a photomicrograph of a coating agent according to the present invention.

On the other hand, FIG. 3 is a photomicrograph of the coating agent according to the present embodiment. When the amounts of a quaternary ammonium salt and phosphoric acid are adjusted so as to have proportions as described above, as a result, it can be seen that only a significantly small amount of precipitate is acknowledged and the defective appearance of the coating film is eliminated as is apparent from FIG. 3.

In addition, the proportion of the polyvalent carboxylic acid contained in the antibacterial/antiviral coating agent according to the present embodiment varies depending on the number of carboxyl groups of the polyvalent carboxylic acid, and the like, but it is preferable that the quaternary ammonium salt:polyvalent carboxylic acid=1:0.01 to 1:0.5 in a mole ratio of the quaternary ammonium salt to the polyvalent carboxylic acid. When the amount of quaternary ammonium salt is large and the amount of polyvalent carboxylic acid is small, it is impossible to sufficiently obtain the effect of improving the water resistance by concurrent use of a polyvalent carboxylic acid in some cases.

[Other Components]

The antibacterial/antiviral coating agent of the present embodiment may be one containing a quaternary ammonium salt, a polyvalent carboxylic acid, and phosphoric acid in an acrylic melamine paint, and it may contain other components and the like if necessary as long as the effect of the present embodiment is not impaired.

[Method of Preparing Antibacterial/Antiviral Coating Agent]

The antibacterial/antiviral coating agent of the present embodiment is prepared, for example, as follows. First, a quaternary ammonium salt and a polyvalent carboxylic acid are weighed, added to a thinner, and stirred for a predetermined time to be completely dissolved. Next, phosphoric acid is weighed and added to the thinner solution dropwise while stirring is continued and the mixture is stirred in a sealed state in order to prevent solvent volatilization. Subsequently, the thinner solution thus prepared is added to an acrylic melamine paint being stirred in the sealed state, whereby the antibacterial/antiviral coating agent is prepared. Incidentally, the amount of the quaternary ammonium salt added at this time is calculated as the parts by mass when the solids in the acrylic melamine paint is taken as 100 parts by mass and determined to be within the above range. In addition, the amounts of the polyvalent carboxylic acid and phosphoric acid added are calculated as the mole ratios with respect to the quaternary ammonium salt based on the number of moles of the quaternary ammonium salt and determined to be within the above ranges.

[Method of Forming Antibacterial/Antiviral Coating Film]

With regard to the method of forming an antibacterial/antiviral coating film of the present embodiment, the antibacterial/antiviral coating film is formed by attaching the antibacterial/antiviral coating agent of the present embodiment described above onto an object to be treated and then subjecting the coating agent to a heat treatment.

The method of attaching the antibacterial/antiviral coating agent of the present embodiment to the surface to be treated is not particularly limited, and it may be a coating method such as brush coating or spray coating or a method in which the object to be treated is directly immersed in the antibacterial/antiviral coating agent of the present embodiment for a predetermined time.

In addition, when the temperature for heat treatment after the antibacterial/antiviral coating agent is attached onto the object to be treated is too low, the coating agent cannot be sufficiently cured and it is thus impossible to form an antibacterial/antiviral coating film exhibiting excellent water resistance due to ionic bonding between a quaternary ammonium salt and a polyvalent carboxylic acid. When the temperature is too high, there is a possibility to cause thermal degradation of the antibacterial/antiviral treated surface and the object to be treated. Hence, this temperature for heat treatment varies depending on the kind of acrylic melamine paint to be used as well, but it is preferably from 150 to 170° C. and more preferably from 155 to 165° C. The time for heat treatment varies depending on the temperature for heat treatment as well, but it is preferably from 20 to 40 minutes and particularly preferably from 25 to 35 minutes.

Incidentally, prior to the formation of the antibacterial/antiviral coating film, a primer layer or an intermediate coating film as described in Patent Document 2 mentioned above may be formed on the surface to be treated if necessary.

The film thickness of the antibacterial/antiviral coating film of the present embodiment thus formed is not particularly limited, it varies depending on the application of the member to which this antibacterial/antiviral coating film is applied and the presence or absence of the ground layer as well, but it is usually set to about from 10 to 30 When the film thickness is too thin, the durability of the coating film is inferior. When the film thickness is too thick, it is concerned that the coating film peels off and it is uneconomical since the amount of paint to be used is large.

The member to which the antibacterial/antiviral coating film of the present embodiment can be applied is not particularly limited, and for example, the antibacterial/antiviral coating film can be applied to a wide range of members such as interior and exterior building members such as handrails, fittings, knobs of fittings, door pulls, and hand holds; parts such as faucet handle of kitchen, washroom, bathroom, toilet, and the like; stationery, and other daily necessities. The antibacterial/antiviral coating film of the present embodiment exhibits excellent surface hardness and adhesive properties, and thus it does not peel off but is preferably used even when being applied to sliding members such as crescent lock among them. In addition, the substrate can also be a molded member or processed member of a metal, a resin, wood, glass, ceramic, or the like. Examples of the molded member may include extruded materials of aluminum and a resin, casted products of aluminum and iron, and injection molded products of resins, and examples of the processed member may include pressed products.

According to the antibacterial/antiviral coating agent of the present embodiment described above, the following effects are exerted. In other words, the antibacterial/antiviral coating agent in the present embodiment contains an acrylic melamine paint, a quaternary ammonium salt, a polyvalent carboxylic acid, and phosphoric acid. The quaternary ammonium salt is contained at over 3.0 parts by mass and under 5.0 parts by mass and preferably from 3.5 to 4.5 parts by mass with respect to 100 parts by mass of the solids in the paint, and the coating film formed from the coating agent thus exhibits antibacterial/antiviral properties. In addition, phosphoric acid is contained at from 0.5 to 3.5 and preferably from 0.75 to 1.77 in a mole ratio with respect to the quaternary ammonium salt, and thus it is possible to suppress poor curing due to the addition of a quaternary ammonium salt, the coating film exhibits excellent surface hardness and solvent resistance, and the coating film also has a favorable appearance. In addition, the coating agent contains a polyvalent carboxylic acid, and thus the polyvalent carboxylic acid and the quaternary ammonium salt form an ionically bonded body to prevent dissolution out of the quaternary ammonium salt and to exhibit excellent water resistance.

It should be noted that the present invention is not limited to the embodiments described above, and modifications and improvements within a range in which the object of the present invention can be achieved are included in the present invention.

EXAMPLES

Hereinafter, the present invention will be described in more detail based on Examples, but the present invention is not limited by these Examples.

Examples 1 to 15 and Comparative Examples 1 to 20

The antibacterial/antiviral coating agents of Examples 1 to 15 and Comparative Examples 1 to 20 were prepared by the following method. At the proportions presented in Table 2, a quaternary ammonium salt ("Catinal STC-80" manufactured by TOHO Chemical Industry Co., Ltd.) and trimesic acid (manufactured by TOKYO CHEMICAL INDUSTRY CO., LTD.) were weighed, added to a thinner ("Kanpe Baking Thinner No. 5" manufactured by KANSAI PAINT CO., LTD.), and stirred for 15 minutes or longer by using a magnetic stirrer to be completely dissolved. Incidentally, the subsequent operations were conducted in a sealed state in order to prevent solvent volatilization. In addition, while stirring was continued, phosphoric acid (manufactured by KANTO CHEMICAL CO., INC.) was weighed in an amount presented in Table 2 and added to the solution dropwise, and the mixture was stirred for 15 minutes or longer. Finally, the thinner solution prepared above was added to an acrylic melamine paint ("MAGICRON 1026" manufactured by KANSAI PAINT CO., LTD.) while stirring the paint by using a magnetic stirrer. Stirring was conducted for 15 minutes or longer. Incidentally, the amount of the quaternary ammonium salt added was calculated as the parts by mass when the solids in the acrylic melamine paint was taken as 100 parts by mass and the amounts of the trimesic acid and phosphoric acid added were determined by calculating the mole ratios thereof to the quaternary ammonium salt based on the number of moles of the quaternary ammonium salt.

The antibacterial/antiviral coating agent thus prepared was applied by the following method to fabricate a coating film. First, as a coating substrate, an aluminum plate degreased by being immersed in acetone for 4 minutes was used. Next, a primer ("Nippe Power Bind" manufactured by NIPPON PAINT CO., LTD.) and a special thinner were mixed, spray-applied on the substrate, and then held at room temperature for 4 minutes. Furthermore, a metallic paint ("Super Lac Neo" manufactured by NIPPON PAINT CO., LTD.) and a special thinner were mixed, spray-applied thereon as an upper layer, and then held at room temperature for 4 minutes. Thereafter, the resultant was baked in an electric furnace at 150° C. for 15 minutes to be cured, thereby forming a primer layer and an intermediate layer. The primer layer and the intermediate coating layer were adjusted so as to have a film thickness of from 10 to 15 μm, respectively. In addition, the antibacterial/antiviral coating agent was further spray-applied on an upper layer of the primer layer and the intermediate layer, then held at room temperature for 4 minutes, and then baked in an electric furnace at 165° C. for 20 minutes to be cured, thereby forming an antibacterial/antiviral coating layer. The antibacterial/antiviral coating layer was adjusted so as to have a film thickness of from 10 to 15 μm.

TABLE 02

|  | Acrylic melamine paint Parts by mass | Quaternary ammonium salt Parts by mass | Phosphoric acid (quaternary ammonium salt ratio) Mole ratio | Trimesic acid (quaternary ammonium salt ratio) Mole ratio |
|---|---|---|---|---|
| Comparative Example 1 | 100.0 | 7.5 | 0.76 | 0.114 |
| Comparative Example 2 | 100.0 | 6.5 | 1.29 | 0.110 |
| Comparative Example 3 | 100.0 | 6.5 | 0.75 | 0.112 |
| Comparative Example 4 | 100.0 | 5.0 | 2.42 | 0.109 |
| Comparative Example 5 | 100.0 | 5.0 | 1.64 | 0.109 |
| Comparative Example 6 | 100.0 | 5.0 | 0.74 | 0.107 |
| Comparative Example 7 | 100.0 | 5.0 | 0.74 | 0.000 |
| Comparative Example 8 | 100.0 | 5.0 | 0.74 | 0.502 |
| Comparative Example 9 | 100.0 | 5.0 | 0.39 | 0.112 |
| Comparative Example 10 | 100.0 | 5.0 | 0.00 | 0.112 |
| Example 1 | 100.0 | 4.5 | 2.24 | 0.111 |
| Example 2 | 100.0 | 4.5 | 1.37 | 0.121 |
| Example 3 | 100.0 | 4.5 | 0.83 | 0.160 |
| Example 4 | 100.0 | 4.0 | 3.01 | 0.109 |
| Example 5 | 100.0 | 4.0 | 1.77 | 0.109 |
| Example 6 | 100.0 | 4.0 | 1.50 | 0.109 |
| Example 7 | 100.0 | 4.0 | 0.91 | 0.106 |
| Example 8 | 100.0 | 4.0 | 0.75 | 0.112 |
| Example 9 | 100.0 | 4.0 | 0.75 | 0.504 |
| Comparative Example 11 | 100.0 | 4.0 | 0.75 | 0.000 |
| Comparative Example 12 | 100.0 | 4.0 | 0.38 | 0.109 |
| Comparative Example 13 | 100.0 | 4.0 | 0.16 | 0.109 |
| Comparative Example 14 | 100.0 | 4.0 | 0.00 | 0.109 |
| Example 10 | 100.0 | 3.5 | 2.82 | 0.109 |
| Example 11 | 100.0 | 3.5 | 2.46 | 0.109 |
| Example 12 | 100.0 | 3.5 | 2.01 | 0.141 |
| Example 13 | 100.0 | 3.5 | 1.73 | 0.203 |
| Example 14 | 100.0 | 3.5 | 1.39 | 0.125 |
| Example 15 | 100.0 | 3.5 | 1.05 | 0.201 |
| Comparative Example 15 | 100.0 | 3.0 | 2.01 | 0.110 |
| Comparative Example 16 | 100.0 | 3.0 | 0.72 | 0.110 |
| Comparative Example 17 | 100.0 | 3.0 | 0.21 | 0.110 |
| Comparative Example 18 | 100.0 | 2.0 | 1.83 | 0.106 |
| Comparative Example 19 | 100.0 | 2.0 | 0.75 | 0.112 |
| Comparative Example 20 | 100.0 | 2.0 | 0.00 | 0.106 |

The antibacterial/antiviral coating agents of Examples 1 to 15 and Comparative Examples 1 to 20 were subjected to the following evaluation, and the results are presented in Table 3.

Evaluation on antiviral properties and antibacterial properties was conducted according to the following evaluation methods. Incidentally, for each of Examples and Comparative Examples, a water resistance test to hold the coating agent in pure water at 25±2° C. for 16 hours was conducted to evaluate the antibacterial properties and the antiviral properties at the initial stage and after the test.

[Antiviral Properties]

An antiviral test was conducted with reference to the antibacterial test method (JIS Z 2801). The bacteria to be tested were influenza A virus (H1N1). Specifically, a test piece (5 cm×5 cm) was placed in a moisture-retained petri dish, 0.2 mL of the virus culture was inoculated onto the test piece, the upper surface was further covered with a 4-cm square polypropylene film to increase the contact efficiency between the virus and the test piece, and the virus was allowed to act at room temperature for 20 minutes. After the action, the test piece was placed in a styrene case, 10 mL of phosphate buffered saline was added thereto, and the styrene case was shaken for 3 minutes to elicit the virus. This solution was used as a stock solution of a sample for virus infectivity measurement. In addition, the virus culture was also inoculated onto a control product which was fabricated by using an aluminum plate and had the same size with the test piece instead of the test piece in the same manner. The virus infectivity values immediately after the inoculation and after 20 minutes of the inoculation time were measured in the same manner as the test piece by the following measurement method.

(Method of Measuring Virus Infectivity Value)

The stock solution of the sample for virus infectivity measurement was serially diluted 10-fold with phosphate buffered saline, and then 50 µL of the stock solution of the sample for measurement or the diluted virus culture and 50 µL of Madin-Darby canine kidney (MDCK) cells suspended in Dulbecco's modified Eagle's Medium (DMEM) containing 5% fetal bovine serum were implanted in a 96-well plate and incubated for 4 days in a carbonic acid gas incubator. After the incubation, the cytopathic effect was confirmed under a microscope, the virus infectivity value test was conducted by the Reed-Muench method, and the infectivity value was determined by the TCID 50 method. The virus inactivation rate of each test piece was calculated according to the following formula.

$$\text{Virus inactivation rate} = (1 - \text{infectivity value of test piece}/\text{infectivity value of control product}) \times 100\% \quad [\text{Math 01}]$$

As the evaluation on antiviral properties, it was evaluated to exhibit antiviral properties when the virus inactivation rate was 99% or more at the initial stage and 90% or more after the water resistance test and not to exhibit antiviral properties when the virus inactivation rate was under 99% at the initial stage or under 90% after the water resistance test.

[Antibacterial Properties]

An antibacterial test was conducted with reference to JIS Z 2801. *Escherichia coli* (NBRC 3972) was used as the bacteria to be tested. Specifically, a test piece (5 cm×5 cm) was placed in a sterilized petri dish, 0.4 mL of an inoculating bacterial culture was inoculated onto the test product, and the upper surface of the test piece was further covered with a 4-cm square polypropylene film. This was placed in a desiccator at a temperature of 35±1° C. and an RH of 90% or more, and the viable cell count after 20 minutes of the contact time was measured by the following measurement method. In addition, the inoculating bacterial culture was also inoculated onto a control product which was fabricated by using an aluminum plate and had the same size with the test piece instead of the test piece in the same manner. The viable cell counts immediately after the inoculation and after 20 minutes of the inoculation time were measured in the same manner as the test piece by the following measurement method.

(Method of Measuring Viable Cell Count)

Both the polypropylene film and the test piece were placed in a sterilized plastic bag for stomacher, 10 mL of SCDLP medium was added thereto, and the test bacteria were washed out with a hand or a stomacher. The viable cell count in 1 mL of this washout solution was measured by the SCDLP agar medium pouring method (after incubation at a temperature of 35±1° C. for from 40 to 48 hours). The viable cell count was converted into the value per 1 cm² of the test piece. The antibacterial activity value of each test piece was calculated according to the following formula.

$$\text{Antibacterial activity value} = \text{logarithmic value of viable cell count after 20 min of control product} - \text{logarithmic value of viable cell count after 20 min of test piece} \quad [\text{Math 02}]$$

In addition, the antibacterial properties of each sample after being held in pure water at 25±2° C. for 16 hours was evaluated by the same method and it was adopted as the evaluation results after the water resistance test. The results are presented in Table 3.

Figure 4:
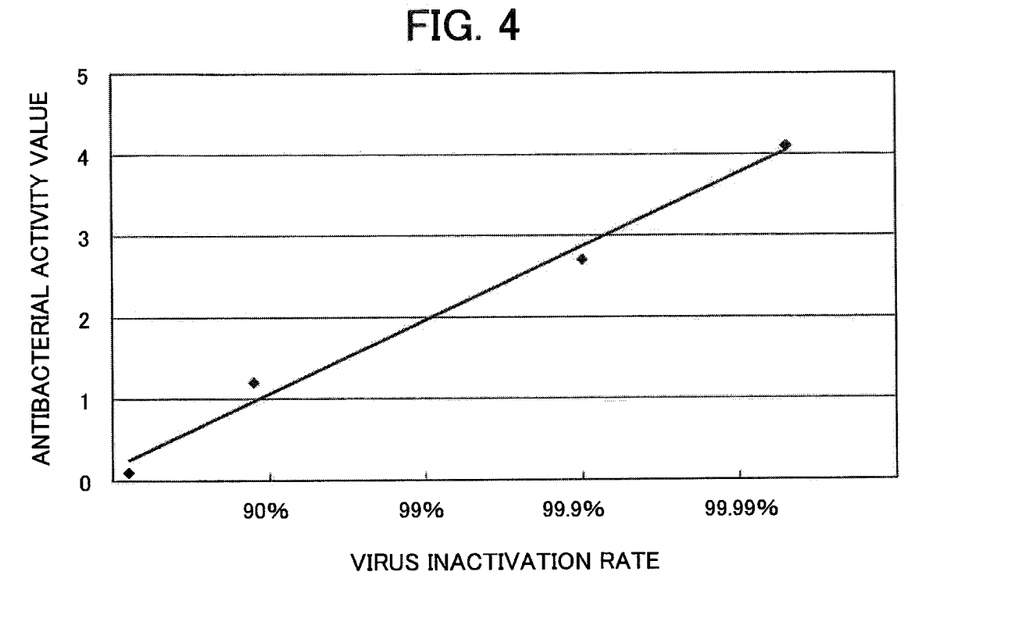
FIG. 4 is a graph illustrating the correlation between the virus inactivation rate and the antibacterial activity value.

Incidentally, in the present Example, the antibacterial activity value was partly adopted as an alternate index of the virus inactivation rate. Here, it has been conventionally known that a quaternary ammonium salt exhibits antiviral properties together with antibacterial properties. FIG. 4 is a graph illustrating the correlation between the virus inactivation rate and the antibacterial activity value. As illustrated in FIG. 4, the correlation between the virus inactivation rate and the antibacterial activity value is high. Hence, it can be seen that it is possible to utilize the antibacterial activity value as an alternate index of the antiviral properties. Based on the correlation between the virus inactivation rate and the antibacterial activity value, it was evaluated to exhibit antibacterial/antiviral properties when the antibacterial activity value was 2.0 or more at the initial stage and 1.0 or more after the water resistance test and not to exhibit antibacterial/antiviral properties when the antibacterial activity value was under 2.0 at the initial stage or under 1.0 after the water resistance test. The results are presented in Table 3.

[Appearance of Coating Film]

The appearance of the coating film was evaluated by the following method. The surface of the coating film was observed through a microscope (metallic microscope "BX 41 M-LED" manufactured by Olympus Corporation, magnification: 100-fold (eyepiece: 10-fold, objective: 10-fold)) to count foreign substances having a diameter of 30 µm or more. The appearance was evaluated to be acceptable (2) in a case in which foreign substances having a diameter of 150 µm or more were fewer than 30 pieces per unit area (1 cm²) and to be unacceptable (1) in a case in which foreign substances having a diameter of 150 µm or more were 30 pieces or more per unit area (1 cm²). The results are presented in Table 3.

[Solvent Resistance (Rubbing Test)]

A rubbing test was conducted by the following method. First, the surface of the coating film was strongly rubbed 5 times with a waste cloth impregnated with ethanol, and the appearance of the coating film after ethanol evaporated was visually observed. The solvent resistance was evaluated to be unacceptable (1) in a case in which there were changes in the appearance such as a decrease in gloss and dissolution of the coating film and to be acceptable (2) in a case in which there was no change in appearance. The results are presented in Table 3.

[Surface Hardness (Pencil Hardness Test)]

A pencil hardness test was conducted by the following method. First, a pencil ("Hi-uni" manufactured by MITSUBISHI PENCIL CO., LTD.) was polished with #400 sandpaper so that the lead tip thereof became even. Thereafter, the pencil was brought into contact with the test surface at an angle of 45°, the sample was extruded forward at a speed of 1 cm/s to scratch the coated surface while pressing the pencil as strongly as possible to an extent to which the lead was not broken, and the presence or absence of scratches was visually judged. The test was conducted 5 times, and the highest hardness at which the coated surface was not scratched all the 5 times of test was recorded and adopted as the pencil hardness. The surface hardness was evaluated to be unacceptable (1) in a case in which the pencil hardness was B or lower and to be acceptable (2) in a case in which the pencil hardness was HB or higher. The results are presented in Table 3.

[Cross-Cut Adhesion Test]

A cross-cut adhesion test was conducted by the following procedure with reference to former JIS K 5400. First, 11 cuts (1 mm interval) to reach the substrate were made on the surface of the coating film by using a cutter. Incidentally, the cuts were made by using a cutter guide so as to be parallel to each other. Next, 11 cuts orthogonal to the cuts previously made were made in the same manner, thereby fabricating 100 squares of 1-mm square (cross-cut) in total. Next, a cellophane tape (registered trademark, manufactured by NICHIBAN CO., LTD.) was allowed to strongly adhere to the cross-cut portion prepared as described above, and the end of the tape was held and vigorously peeled off therefrom at an angle of 45°. The number of remaining squares was counted and adopted as the test result. The coating film was evaluated to be acceptable when the number of remaining squares was 100, and the results are presented in Table 3.

TABLE 03

| | Number of foreign substances pieces/cm² | Evaluation on appearance | Virus inactivation rate - Initial stage | Virus inactivation rate - After water resistance test | Antibacterial activity value - Initial stage | Antibacterial activity value - After water resistance test | Evaluation on antibacterial/antiviral properties | Rubbing test (evaluation on solvent resistance) | Pencil hardness | Evaluation on surface hardness | Evaluation by cross-cut adhesion test |
|---|---|---|---|---|---|---|---|---|---|---|---|
| Comparative Example 1 | 352 | 1 | — | — | 4.3 | 4.3 | 2 | 2 | H | 2 | 100 |
| Comparative Example 2 | 211 | 1 | — | — | 4.3 | 3.1 | 2 | 2 | F | 2 | 100 |
| Comparative Example 3 | 211 | 1 | — | — | 4.3 | 4.3 | 2 | 2 | F | 2 | 100 |
| Comparative Example 4 | 563 | 1 | — | — | 4.3 | 4.3 | 2 | 2 | H | 2 | 100 |
| Comparative Example 5 | 282 | 1 | — | — | 4.3 | 4.3 | 2 | 2 | H | 2 | 100 |
| Comparative Example 6 | 225 | 1 | — | — | 4.3 | 4.3 | 2 | 2 | F | 2 | 100 |
| Comparative Example 7 | 102 | 1 | — | — | 4.3 | 0.0 | 1 | 2 | H | 2 | 100 |
| Comparative Example 8 | 145 | 1 | — | — | 4.3 | 2.5 | 1 | 2 | H | 2 | 100 |
| Comparative Example 9 | 113 | 1 | — | — | 4.3 | 1.6 | 2 | 2 | HB | 1 | 100 |
| Comparative Example 10 | 0 | 2 | — | — | 4.3 | 0.0 | 1 | 1 | 2B | 1 | 100 |
| Example 1 | 0 | 2 | — | — | 4.3 | 1.1 | 2 | 2 | H | 2 | 100 |
| Example 2 | 0 | 2 | — | — | 4.3 | 1.2 | 2 | 2 | H | 2 | 100 |
| Example 3 | 0 | 2 | — | — | 4.3 | 1.3 | 2 | 2 | H | 2 | 100 |
| Example 4 | 0 | 2 | — | — | 4.3 | 4.3 | 2 | 2 | H | 2 | 100 |
| Example 5 | 0 | 2 | — | — | 4 | 4.3 | 2 | 2 | F | 2 | 100 |
| Example 6 | 0 | 2 | — | — | 4.3 | 3.7 | 2 | 2 | F | 2 | 100 |
| Example 7 | 0 | 2 | — | — | 4.3 | 4.3 | 2 | 2 | H | 2 | 100 |
| Example 8 | 0 | 2 | 99.9 | 94.6 | 4.3 | 2.8 | 2 | 2 | H | 2 | 100 |
| Example 9 | 0 | 2 | — | — | 4.1 | 2.0 | 2 | 2 | H | 2 | 100 |
| Comparative Example 11 | 0 | 2 | — | — | 4.1 | 0.0 | 1 | 2 | B | 1 | 100 |
| Comparative Example 12 | 0 | 2 | — | — | 4.3 | 0.9 | 1 | 1 | H | 2 | 100 |
| Comparative Example 13 | 0 | 2 | — | — | 4.3 | 0.1 | 1 | 2 | B | 1 | 100 |
| Comparative Example 14 | 0 | 2 | — | — | 4.3 | 0.0 | 1 | 2 | H | 2 | 100 |
| Example 10 | 28 | 2 | — | — | 4.3 | 4.3 | 2 | 2 | F | 2 | 100 |
| Example 11 | 0 | 2 | — | — | 4.3 | 3.5 | 2 | 2 | HB | 2 | 100 |
| Example 12 | 0 | 2 | — | — | 4.3 | 3.3 | 2 | 2 | HB | 2 | 100 |
| Example 13 | 0 | 2 | — | — | 4.3 | 2.5 | 2 | 2 | F | 2 | 100 |
| Example 14 | 0 | 2 | 99.9 | 92.6 | 4.3 | 2.6 | 2 | 2 | H | 2 | 100 |
| Example 15 | 0 | 2 | — | — | 4.3 | 1.5 | 2 | 2 | HB | 2 | 100 |
| Comparative Example 15 | 0 | 2 | — | — | 4.3 | 0.0 | 1 | 2 | F | 2 | 100 |
| Comparative Example 16 | 0 | 2 | — | — | 4.3 | 0.2 | 1 | 2 | HB | 2 | 100 |
| Comparative Example 17 | 0 | 2 | — | — | 0.3 | 0.1 | 1 | 1 | HB | 2 | 100 |
| Comparative Example 18 | 0 | 2 | — | — | 4.3 | 0.0 | 1 | 2 | HB | 2 | 100 |
| Comparative Example 19 | 0 | 2 | — | — | 4 | 0.1 | 1 | 2 | F | 2 | 100 |
| Comparative Example 20 | 0 | 2 | — | — | 0 | 0.0 | 1 | 1 | HB | 2 | 100 |

Figure 5:
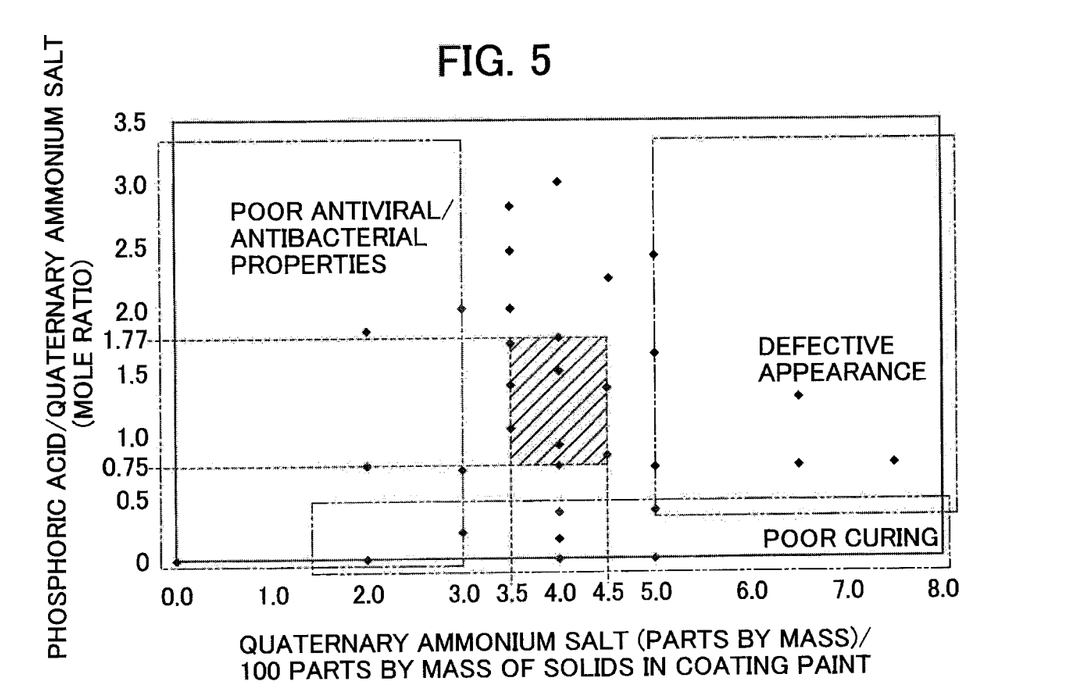
FIG. 5 is a graph illustrating the relation between the amounts of a quaternary ammonium salt and phosphoric acid added and the respective evaluation results.

FIG. 5 is a graph illustrating the relation between the amount of the quaternary ammonium salt with respect to the solids in the paint and the mole ratio of phosphoric acid to the quaternary ammonium salt and the respective evaluation results in Examples based on the results in Table 3. In FIG. 5, the vertical axis represents the mole ratio of phosphoric acid to the quaternary ammonium salt, and the horizontal axis represents the amount (parts by mass) of the quaternary ammonium salt with respect to 100 parts by mass of the solids in the paint. The fact that the coating film formed from the antibacterial/antiviral coating agent according to the present Example exhibits antibacterial/antiviral properties, has a high surface hardness, exhibits solvent resistance, and also has an excellent appearance even after being subjected to the water resistance test will be described in detail below with reference to Table 3 and FIG. 5.

First, when Examples 1 to 15 and Comparative Examples 15 to 20 are compared to each other, the antibacterial/antiviral properties are deteriorated in Comparative Examples 15 to 20 in which the parts by mass of the quaternary ammonium salt with respect to 100 parts by mass of the solids in the paint is 3.0 parts by mass or less. From this result, it has been confirmed that the parts by mass of the quaternary ammonium salt with respect to 100 parts by mass of the solids in the paint is preferably over 3.0 parts by mass.

In addition, when Examples 1 to 15 and Comparative Examples 1 to 9 are compared to each other, a large number of foreign substances are generated in the antibacterial/antiviral coating agent and the appearance of the coating film is deteriorated in Comparative Examples 1 to 9 in which the parts by mass of the quaternary ammonium salt with respect to 100 parts by mass of the solids in the paint is 5.0 mass or more and phosphoric acid is contained in the antibacterial/antiviral coating agent. From this result, it has been confirmed that the parts by mass of the quaternary ammonium salt with respect to 100 parts by mass of the solids in the paint is preferably under 5.0 parts by mass in a case in which phosphoric acid is contained in the antibacterial/antiviral coating agent.

In addition, when Examples 1 to 15 and Comparative Examples 9, 10, 12 to 14, 17, and 20 are compared to each other, the curing of the coating film is insufficient and the solvent resistance and the surface hardness are thus inferior in Comparative Examples 9, 10, 12 to 14, 17, and 20 in which the mole ratio of phosphoric acid to the quaternary ammonium salt is under 0.5. From this result, it has been confirmed that the mole ratio of phosphoric acid to a quaternary ammonium salt is preferably 0.5 or more.

In addition, from the results on the cross-cut adhesion test of Examples and Comparative Examples, it has been confirmed that the antibacterial/antiviral coating agent of the present embodiment exhibits the same favorable adhesive properties as the conventional coating agent and it can be thus used in the same manner as the conventional products without problems.

The invention claimed is:

1. An antibacterial and antiviral coating agent comprising:
    an acrylic melamine paint,
    a quaternary ammonium salt,
    a polyvalent carboxylic acid, and
    phosphoric acid, wherein
    the quaternary ammonium salt is contained at over 3.5 parts by mass and under 4.5 parts by mass with respect to 100 parts by mass of solids in the acrylic melamine paint,
    phosphoric acid is contained at from 0.75 to 1.77 in a mole ratio with respect to the quaternary ammonium salt,
    the quaternary ammonium salt is at least any one of dodecyltrimethylammonium chloride, hexadecyltrimethylammonium chloride, and octadecyltrimethylammonium chloride, and
    the polyvalent carboxylic acid is trimesic acid.

2. The antibacterial and antiviral coating agent according to claim 1, wherein the quaternary ammonium salt is contained at from 4.0 to 4.5 parts by mass with respect to 100 parts by mass of solids in the acrylic melamine paint.

3. The antibacterial and antiviral coating agent according to claim 1, wherein phosphoric acid is contained at from 0.91 to 1.50 in a mole ratio with respect to the quaternary ammonium salt.

4. The antibacterial and antiviral coating agent according to claim 2, wherein phosphoric acid is contained at from 0.91 to 1.50 in a mole ratio with respect to the quaternary ammonium salt.

* * * * *